(12) United States Patent
Swain

(10) Patent No.: US 7,067,161 B2
(45) Date of Patent: Jun. 27, 2006

(54) ANIMAL FOOD SUPPLEMENT COMPOSITIONS AND METHODS OF USE

(76) Inventor: Gayle Dorothy Swain, 7154 W. State St., Boise, ID (US) 83714

( * ) Notice: Subject to any disclaimer, the term of this patent is extended or adjusted under 35 U.S.C. 154(b) by 0 days.

(21) Appl. No.: 10/636,331

(22) Filed: Aug. 6, 2003

(65) Prior Publication Data

US 2004/0241257 A1    Dec. 2, 2004

(30) Foreign Application Priority Data

May 29, 2003   (AU)   ............................... 2003204441

(51) Int. Cl.
*A61K 35/78*   (2006.01)
(52) U.S. Cl. ..................... 424/738; 424/439; 424/442
(58) Field of Classification Search ................ 424/738, 424/439, 442
See application file for complete search history.

(56) References Cited

U.S. PATENT DOCUMENTS

| 4,588,589 | A | * | 5/1986 | Sheth et al. | |
|---|---|---|---|---|---|
| 5,009,916 | A | * | 4/1991 | Colliopoulos | ............... 426/615 |
| 5,120,362 | A | * | 6/1992 | Kauffman | |
| 5,232,699 | A | * | 8/1993 | Colliopoulos | |
| 5,464,644 | A | * | 11/1995 | Wullschleger et al. | |
| 5,656,312 | A | * | 8/1997 | Erasmus et al. | ............... 426/89 |
| 6,042,857 | A | * | 3/2000 | Jones et al. | ................. 428/106 |
| 6,451,370 | B1 | * | 9/2002 | Anderson | ................... 426/635 |

FOREIGN PATENT DOCUMENTS

| WO | WO 98/39980 | 9/1998 |
|---|---|---|
| WO | WO 98/43493 | 10/1998 |
| WO | WO 02/26213 A1 | 4/2002 |

OTHER PUBLICATIONS

Castleman (The Healing Herbs (1991), Rodale Press: Pennsylvania, pp. 37-39).*
Twin Valley Agri-Products, "Psylhusk Pellets," Dec. 2002, 2 pages.
Twin Valley Agri-Products, "Psylhusk Pellets," Apr. 2003, 2 pages.

* cited by examiner

*Primary Examiner*—Susan D. Coe
(74) *Attorney, Agent, or Firm*—TraskBritt

(57) ABSTRACT

An animal food supplement particularly useful in treating gastrointestinal problems, such as colic. Psyllium husks are provided in dry form for convenience of handling prior to feeding. In exemplary embodiments, psyllium husks are admixed with binding material and the admixture is formed into pellets, crumbles, mashes, or licks. Upon consumption by the animal, the psyllium husks take up water from the moist environment of the animal's gastrointestinal tract and form a gelatinous bolus that sweeps through the gastrointestinal tract of the animal, clearing the gastrointestinal tract of intestinal detritus, such as sand, toxins, and microorganisms, which agglomerate with and/or are carried away by the psyllium husk gel.

12 Claims, 3 Drawing Sheets

ANIMAL FOOD SUPPLEMENT COMPOSITIONS AND METHODS OF USE

BACKGROUND OF THE INVENTION

The present invention relates to animal food supplement compositions and methods of using the same, the compositions being particularly useful in relation to, but not limited to, treatment of colic and other gastrointestinal problems in animals.

Animal healthcare is an important consideration in many aspects of the economy, such as in food production, research, education (e.g., in zoos) and animal competitions (e.g., horse racing). Productivity, cost control and profitability in these areas of the economy are improved when the health of the animals involved is improved. Efficient and cost-effective animal healthcare is especially important where a substantial investment is required to raise animals to maturity, as is the case with horses.

Animals frequently ingest sand, soil, and other extraneous materials when they are grazing or feeding from a feed box that contains such contaminants. Over time, deposits of these extraneous materials accumulate in the digestive system of the animal, causing colic. Colic generally refers to malfunction, swelling, infection, or blockage in the gastrointestinal tract of an animal. As used herein, the term "intestinal detritus" refers to the aforementioned ingested sand, soil, and other extraneous materials accumulated in the gastrointestinal tract of an animal.

Instances of colic are particularly distressing for the animal and for the owner, because colic is frequently painful to the animal and difficult to identify and treat. Though an owner may try numerous treatments to relieve the animal's symptoms, unfortunately, previously known treatments often prove ineffective and, unfortunately, animals regularly die as a result of colic. For example, approximately one in ten horses with colic die because no effective treatment has been available in the past.

In economically significant animals such as horses, cattle, swine, chickens, broilers, quail, pheasants, turkeys, ostrich, emus, and other exotic birds, gastrointestinal problems such as colic pose a major economic threat. As a result, means for reducing the economic impact of colic, i.e., cost-effective treatments for colic, are in great demand.

The use of psyllium husk to treat human gastrointestinal problems is well known, but the present inventor is unaware of any previous use of psyllium husk to treat gastrointestinal problems in animals, particularly horses. Thus, when used herein, the term "animal" refers to any nonhuman animal. More particularly, when used herein, the term "animal" is intended to subsume (but not be limited to) horses, cattle, swine, chickens, broilers, quail, pheasants, turkeys, ostrich, emus, and other exotic birds.

The present invention overcomes, at least in part, some of the aforementioned disadvantages of prior art treatments for colic and other gastrointestinal problems in animals.

BRIEF SUMMARY OF THE INVENTION

The present invention provides an animal food supplement particularly useful in treating gastrointestinal problems, such as colic, in horses, cattle, swine, chickens, broilers, quail, pheasants, turkeys, ostrich, emus, and other exotic birds. Psyllium husk is the only natural gelatinous and hygroscopic material that is suitable for consumption by both humans and animals, so it is abundantly available. According to the present invention, psyllium husk may be provided in dry form for convenience of handling prior to feeding. In currently preferred embodiments, psyllium husks may be admixed with binding material having low moisture content, and the admixture is formed into pellets, crumbles, mash, or licks. Upon consumption by the animal, the psyllium husk material takes up water from the moist environment of the animal's gastrointestinal tract and forms a gelatinous bolus that sweeps through the animal's gastrointestinal tract, clearing intestinal detritus, such as sand, soil, toxins, and microorganisms, which agglomerates with and/or is carried away by the psyllium husk gel.

A first aspect of the present invention includes an animal food supplement composition including psyllium husk.

A second aspect of the present invention includes a pharmaceutical composition comprising an animal food supplement composition as an active ingredient optionally admixed with a pharmaceutically acceptable carrier, the animal food supplement composition including psyllium husk.

A third aspect of the present invention includes a method of using an animal food supplement composition for the preparation of medicaments for the treatment of animal gastrointestinal problems, such as horse colic, wherein the animal food supplement composition includes psyllium husk.

A fourth aspect of the present invention includes a packaged animal food supplement composition comprising a substantially hermetic packaging material containing the animal food supplement composition and an atmosphere with a reduced oxygen content in comparison to ambient air.

The present invention advantageously may be incorporated in the ordinary diet of an animal as a treatment for, or preventive measure against, colic and other gastrointestinal problems. An additional advantage of the present invention is that it requires only the use of natural ingredients.

Further advantages of the present invention over the prior art include (but are not limited to) the provision of the animal food supplement according to the invention in a pellet, crumble, mash, or lick form that has a low nutritional value so as to avoid interference with or disruption of the diet of the treated animal and to provide a convenient means by which medication or other dietary supplements, such as vitamins and minerals, may be added to the animal's diet. Through the practice of the present invention, an animal's gastrointestinal tract is cleansed of indigestible matter and toxic deposits for, as appropriate, the prevention and treatment of gastrointestinal problems and improvement of the overall health and well-being of the animal, one result of which is improved economic productivity associated with the animal.

BRIEF DESCRIPTION OF THE SEVERAL VIEWS OF THE DRAWINGS

In the drawings, which illustrate what is currently considered to be the best mode for carrying out the invention.

DETAILED DESCRIPTION OF THE INVENTION

The present invention makes beneficial use of the hygroscopic properties of psyllium husks. Psyllium husks swell when they come into contact with water and thus are difficult to handle conveniently when mixed with conventional animal feeds that have a high moisture content, such as molasses and water. Accordingly, it is preferred to provide psyllium husks in dry form for convenience in handling. Upon consumption by the animal, the psyllium husks take up water from the moist environment of the animal's gastrointestinal tract and form a gelatinous bolus that sweeps through the gastrointestinal tract of the animal, clearing the gastrointestinal tract of intestinal detritus, such as sand, soil, toxins, and microorganisms, which agglomerate with and/or are carried away by the psyllium husk gel.

However, certain animals, such as horses, will not voluntarily eat dry, unbound psyllium husk material because it is unpalatable. Thus, the mere addition of dry unbound psyllium husks to a feed box is ineffective since the animal may never actually consume the psyllium husks despite their inclusion in the feed box. Accordingly, the present invention provides an animal food supplement that is designed to be palatable to animals for which it is intended, e.g., by using flavors, aromas and textures that appeal to the animal to be treated. The selection of flavors, aromas, and textures appropriate for a given subject, i.e., the design of a palatable product, is well within the skill of the ordinary artisan and therefore not discussed further here.

Figure 1:
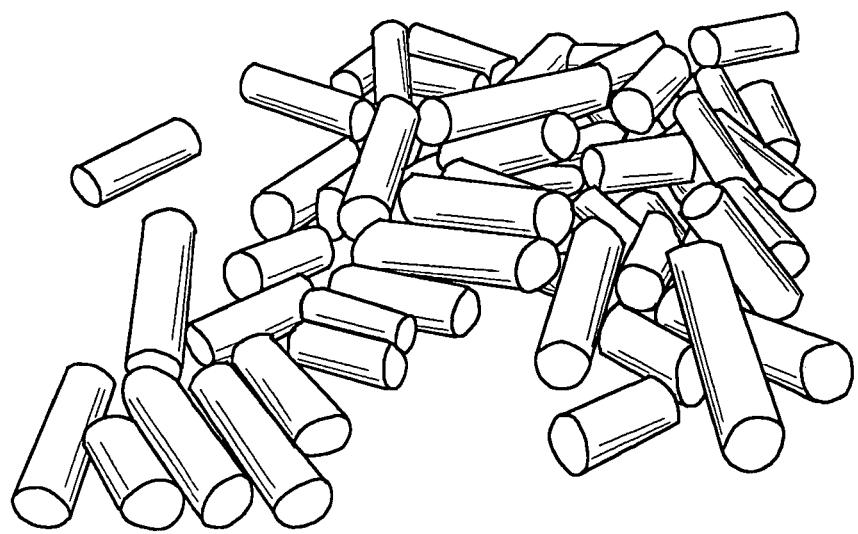
FIG. 1 is a graphical depiction of a pellet physical form of the food supplement composition of the invention.
Figure 2:
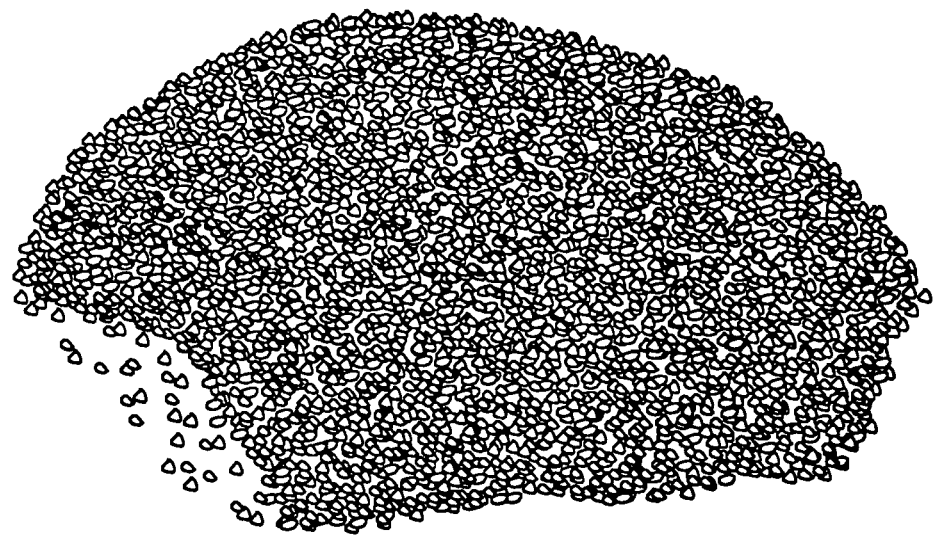
FIG. 2 is a graphical depiction of a crumble physical form of the food supplement composition of the invention.
Figure 3:
FIG. 3 is a graphical depiction of a mash physical form of the food supplement composition of the invention.
Figure 4:
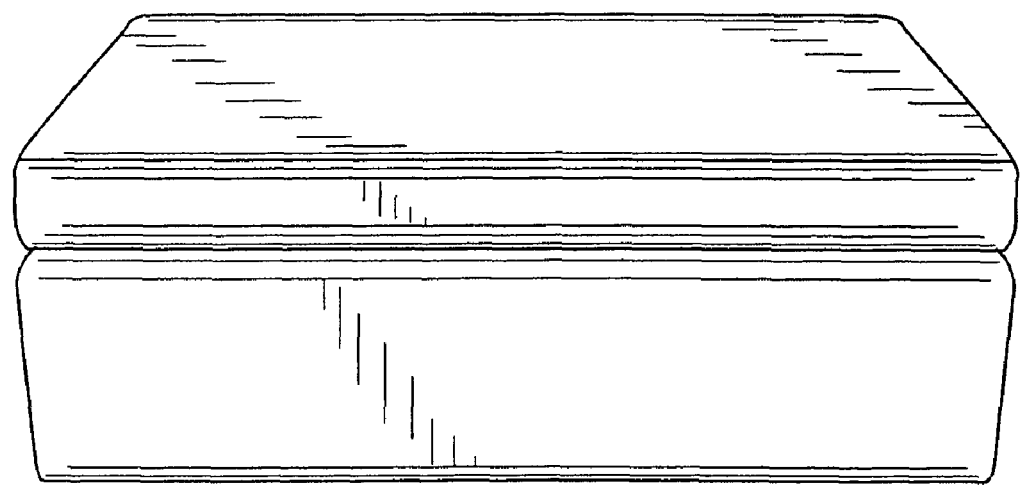
FIG. 4 is a graphical depiction of a lick physical form of the food supplement composition of the invention.

To overcome problems associated with the hygroscopicity of psyllium husks, the present invention provides an animal food supplement prepared from psyllium husks mixed together with a relatively low moisture content binding agent. Preferably, the animal food supplement is extruded into pellet form (as depicted in FIG. 1) for ease of inclusion into the animal's feed box and to ensure consumption thereof by the animal. However, it is also envisaged that the animal food supplement of the invention may be manufactured in a crumble form (as depicted in FIG. 2), a mash form (as depicted in FIG. 3), or an animal lick form (as depicted in FIG. 4).

The animal food supplement of the present invention contains from 0 to about 95 percent by weight of psyllium husks in seed, powdered or granulated form, including particulate material comprising stalk, flower and leaf fragments with up to 0 to about 75 percent impurities. It is currently preferred that the food supplement contain about 50 percent psyllium husks. Most preferably according to present beliefs, the food supplement should contain about 30 to 35 percent psyllium husks.

The animal food supplement of the present invention may also contain from 0 to about 95 percent grain by-products, including oats, barley, maize, lupins, lupin hulls, mill mix, mill run, pollard, bran, canola meal, soya meal in a rolled, crushed or powdered form, or a mixture thereof; from 0 to about 95 percent lucerne in either chaff, hay, fines or powder form, or a mixture thereof; from 0 to about 95 percent oaten, wheaten or meadow hay in chaff, fines or powder form, or a mixture thereof; and/or from 0 to about 95 percent molasses, and, optionally, additional vitamins and minerals.

To avoid interference with or disruption of the animal's diet, the food supplement of the invention preferably contains less than about 8 percent protein.

It is currently preferred that the moisture content of an animal food supplement according to the invention be approximately 11 to 14 percent. It is also currently preferred that an animal food supplement according to the invention contain between about 7.5 and 10 percent lucerne in either chaff, hay, fines or powder form, or a mixture thereof.

Pellets of the animal food supplement of the invention are prepared by rolling, crushing and/or powdering grain by-products and other binding agents as described above to achieve a substantially homogenously sized mixture. Psyllium husks are then added to the mixture, whereupon the mixture is treated with steam and extruded through dies, which may range, for example, from 2 to 10 mm in aperture size to form pellets.

The use of proper packaging of the food supplement of the invention is also a significant consideration. If exposed to ambient air, the flavor, aroma and texture of the supplement degrade undesirably over time. However, vacuum packaging is not suitable because the supplement is best preserved if it is allowed to "breathe" without being exposed to ambient air. Thus, another advantageous aspect of the invention is specialized packaging that prevents or reduces the aforementioned degradation.

Figure 5:
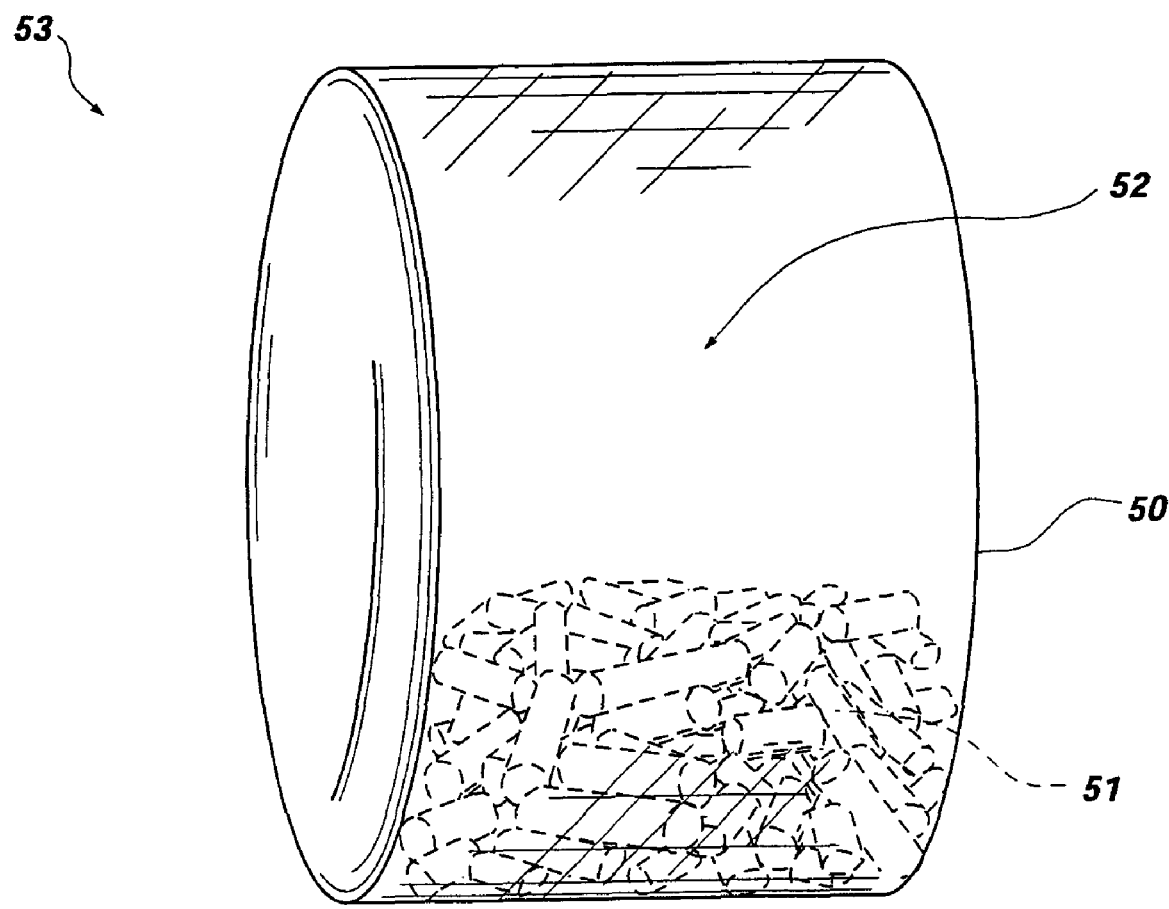
FIG. 5 is a graphical depiction of a specialized package containing the food supplement composition of the invention.

Referring to FIG. 5, the packaging according to the invention is substantially hermetic, and a reduced oxygen content atmosphere such as an inert gas, for example, nitrogen, may be introduced into the package during filling thereof with the supplement in an appropriate form (for example, pellets) to displace ambient air present inside the package, providing a sealed environment, generally indicated at 50, containing the supplement 51 and an atmosphere 52 including less oxygen than ambient air 53. Thus, packaging is provided that allows the food supplement of the invention to "breathe" the atmosphere within the package while preventing or at least reducing the degradation caused by exposure to ambient air. Currently preferred are 3-ply paper sacks, in which one ply is a 40 µm BOPP liner, supplied by Australian Multiwall Bag Co. Pty. Ltd. (Murdoch, Australia).

In use, the animal food supplement composition may be introduced in pellet form, for example, into the feed box of an animal that is exhibiting symptoms of gastrointestinal problems, such as colic. In an exemplary treatment for an adult horse, a dose of about 500 g of the composition is provided on the first day of treatment, a dose of about 850 g of the composition is provided on the second day of treatment, a dose of about 1000 g of the composition is provided on the third day of treatment, a dose of about 2000 g of the composition is provided on the fourth day of treatment, and a final dose of 2500 g of the composition is provided on the fifth day of treatment.

During administration of the food supplement of the present invention, the animal must drink plenty of fresh water on a regular basis, otherwise serious injury may result.

The food supplement of the present invention was tested against a placebo in horses. The feces of the horses were monitored for clearance of intestinal detritus, and x-ray imaging was also used to monitor movement of material through the gastrointestinal tracts of the horses. One group of horses was administered the food supplement of the invention according to the above schedule, while a control group was fed a placebo according to the same schedule. All horses that received the food supplement of the invention cleared accumulated intestinal detritus (sand) during the course of treatment, while those in the placebo group either did not clear or cleared very little intestinal detritus. Horses receiving the food supplement of the invention passed as much as ¼ gallon of sand in feces in a 24-hour period during treatment.

In addition, it was also observed that the general health and performance of the animals were improved after receiving the food supplement of the present invention. After treatment, animals were observed to excrete less undigested feed, the condition of their coats improved, and even some inexplicable behavioral problems were resolved. While not intending to be bound to any particular theory of action, the inventor believes that clearance of intestinal detritus through administration of the food supplement of the present invention is useful in treating not only colic, but also other problems that may be related to gastrointestinal blockage and/or accumulation, such as equine ulcers and founder. Research is ongoing to determine whether equine ulcers are caused by bacteria, as are ulcers in humans. If so, the food supplement of the present invention may be useful in preventing as well as treating equine ulcers by clearing the equine gut of bacterial deposits. Further, it is believed that founder (chronic laminitis) can be caused by toxic accumulations in the caecum, which kill off beneficial bacteria and damage the wall of the caecum. The damaged tissue of the caecum diverts resources such as glucose from the bloodstream as it heals, and founder is believed to result from insufficient nutrient supply to the hoof. Thus, the present invention is likely useful in treating a variety of animal health problems, as well as for promoting and maintaining general gastrointestinal health in animals.

The food supplement of the present invention is useful in horses, cattle, swine, chickens, broilers, quail, pheasants, turkeys, ostrich, emus, and other exotic birds. Of course, it is contemplated that the number of days of treatment and the dosages applied to each of these species will vary depending upon the size of the animal and the severity of the symptoms that it exhibits. For example, weanling and yearling horses may be fed at half the rate of an adult horse, and ponies may be administered a dose of one third cup per day for five days. One of ordinary skill in the art in the health care of a given animal will readily be able to determine an appropriate dosage regimen. In general, it is currently preferred to administer the food supplement of the invention for five days with gradually increasing daily doses.

The above-mentioned treatment schedule, or one similar thereto, may be repeated every ten weeks as a preventive treatment against colic or other gastrointestinal problems.

Surprisingly, the food supplement of the present invention was also discovered to eradicate rodent pests. Rodents that consume the food supplement of the invention die, presumably because the hygroscopic swelling of the psyllium husks blocks or bursts the rodent's gastrointestinal tract. This unexpected benefit of the present invention is particularly advantageous because the same material can be used concurrently to treat gastrointestinal problems in economically significant animals and to eradicate rodent pests.

Although the present invention has been described with respect to the currently preferred embodiments set forth herein, various additions, deletions and modifications are contemplated as being within its scope. The scope of the invention is, therefore, indicated by the ensuing claims, rather than the foregoing description. All changes that come within the meaning and range of equivalency of the claims are to be embraced within their scope.

What is claimed is:

1. A solid food supplement composition for a non-human animal, composing:
   between about 30 to 35 percent psyllium husk material;
   less than about 8 percent protein;
   between about 7.5 to 10 percent lucerne;
   at least one binding agent binding the psyllium husk material in a desired physical form; and
   a moisture content of approximately 11 to 14 percent.

2. The food supplement composition of claim 1, wherein the food supplement composition is sufficiently low in nutritional value so as to avoid interference with or disruption of the diet of the non-human animal ingesting the food supplement composition.

3. The food supplement composition of claim 1, further comprising at least one grain by-product selected from the group consisting essentially of oats, barley, maize, lupins, lupin hulls, bran, canola meal, and soya meal.

4. The food supplement composition of claim 1, further comprising hay.

5. The food supplement composition of claim 4, wherein the hay is at least one of oaten, wheaten, and meadow hay.

6. The food supplement composition of claim 1, further comprising at least one pharmaceutical composition.

7. The food supplement composition of claim 1, further comprising at least one nutrient.

8. The food supplement composition of claim 7, wherein the at least one nutrient is at least one of a vitamin and a mineral.

9. The food supplement composition of claim 1, wherein the desired physical form is a pellet, a crumble, a mash, or a lick.

10. The food supplement composition of claim 1, further comprising a flavoring.

11. The food supplement composition of claim 10, wherein the flavoring includes molasses.

12. A substantially hermetic package containing a solid food supplement composition, the substantially hermetic package containing an atmosphere having less oxygen than ambient air, the solid food supplement composition comprising:
   between about 30 to 35 percent psyllium husk material;
   less than about 8 percent protein;
   between about 7.5 to 10 percent lucerne;
   at least one binding agent for binding the psyllium husk material in a desired physical form; and
   a moisture content of approximately 11 to 14 percent.

* * * * *